(12) United States Patent
Williamson, IV et al.

(10) Patent No.: US 8,877,146 B2
(45) Date of Patent: *Nov. 4, 2014

(54) CASSETTE FOR HANDLING AND HOLDING TISSUE SAMPLES DURING PROCESSING, EMBEDDING AND MICROTOME PROCEDURES, AND METHODS THEREFOR

(75) Inventors: Warren P. Williamson, IV, Loveland, OH (US); Thomas J. Ward, Columbus, OH (US); Stephen P. Whitlatch, Cincinnati, OH (US)

(73) Assignee: Biopath Automation, L.L.C., Loveland, OH (US)

( * ) Notice: Subject to any disclaimer, the term of this patent is extended or adjusted under 35 U.S.C. 154(b) by 1410 days.

This patent is subject to a terminal disclaimer.

(21) Appl. No.: 11/618,987

(22) Filed: Jan. 2, 2007

(65) Prior Publication Data
US 2007/0104618 A1    May 10, 2007

Related U.S. Application Data

(62) Division of application No. 10/963,315, filed on Oct. 12, 2004, now Pat. No. 7,179,424.

(60) Provisional application No. 60/512,147, filed on Oct. 17, 2003.

(51) Int. Cl.
*B01L 9/00* (2006.01)
*B01L 3/00* (2006.01)
*G01N 1/31* (2006.01)

(52) U.S. Cl.
CPC .......... *B01L 3/545* (2013.01); *G01N 2001/315* (2013.01); *G01N 1/31* (2013.01); *B01L 2300/02* (2013.01)
USPC .......................................... 422/561; 422/560

(58) Field of Classification Search
CPC .......................... G01N 1/28; B01L 2300/0609
USPC .......................... 422/102, 82.05, 104; 436/46
See application file for complete search history.

(56) References Cited

U.S. PATENT DOCUMENTS 1,885,138 A    11/1932  Pilson
2,749,909 A     6/1956  Ullery et al.
(Continued)

FOREIGN PATENT DOCUMENTS

EP    0139424 A2    5/1985
EP    0142574 A1    5/1985
(Continued)

OTHER PUBLICATIONS

U.S. Patent and Trademark Office, Office Action in U.S. Appl. No. 11/072,119, Dec. 19, 2008.
(Continued)

*Primary Examiner* — Natalie Levkovich
(74) *Attorney, Agent, or Firm* — Wood, Herron & Evans, L.L.P.

(57) ABSTRACT

A cassette for holding a tissue sample includes a body having a bottom wall and a plurality of side walls extending upwardly with respect to the bottom wall to define an interior space for receiving the tissue sample. A lid is configured to be received in the interior space, and the cassette is sectionable in a microtome. Sensing elements are associated with the body or lid and configured to allow an automated sensing system to determine at least one characteristic of the cassette. A flange extends along upper portions of at least two of the side walls and includes a plurality of holes. Other features are included to more effectively and efficiently manufacture and use the cassette.

10 Claims, 7 Drawing Sheets

(56) References Cited

U.S. PATENT DOCUMENTS

| | | |
|---|---|---|
| 2,776,596 A | 1/1957 | Eigen |
| 2,996,762 A | 8/1961 | McCormick |
| 3,224,434 A | 12/1965 | Molomut et al. |
| 3,257,279 A | 6/1966 | Schain |
| 3,527,863 A | 9/1970 | Weichselbaum |
| 3,587,872 A | 6/1971 | Pauly |
| 3,624,197 A | 11/1971 | Schain |
| 3,679,450 A | 7/1972 | Beightol |
| 3,691,097 A | 9/1972 | Stiles et al. |
| 3,723,061 A | 3/1973 | Stahl |
| 3,777,882 A | 12/1973 | McIntyre |
| 3,814,670 A | 6/1974 | Freake et al. |
| 3,874,851 A | 4/1975 | Wilkins et al. |
| 3,961,097 A | 6/1976 | Gravlee, Jr. |
| 3,982,862 A | 9/1976 | Pickett et al. |
| 3,996,326 A | 12/1976 | Schachet |
| 4,025,306 A | 5/1977 | Studer |
| 4,199,558 A | 4/1980 | Henderson |
| 4,219,334 A | 8/1980 | Schluter et al. |
| 4,220,252 A | 9/1980 | Beall et al. |
| 4,224,277 A | 9/1980 | Macho et al. |
| 4,261,474 A | 4/1981 | Cohen |
| 4,340,066 A | 7/1982 | Shah |
| 4,353,856 A | 10/1982 | Muck et al. |
| 4,427,614 A | 1/1984 | Barham et al. |
| 4,435,507 A | 3/1984 | Stenkvist |
| 4,439,319 A | 3/1984 | Rock |
| 4,446,900 A | 5/1984 | Markovich |
| 4,497,792 A | 2/1985 | Gindler |
| 4,545,831 A | 10/1985 | Ornstein |
| 4,557,903 A | 12/1985 | McCormick |
| 4,569,647 A | 2/1986 | McCormick |
| 4,576,796 A | 3/1986 | McCormick |
| 4,627,129 A | 12/1986 | Wittes |
| 4,656,047 A | 4/1987 | Kok et al. |
| 4,695,339 A | 9/1987 | Rada |
| 4,733,806 A | 3/1988 | Sloop |
| 4,752,347 A | 6/1988 | Rada |
| 4,801,553 A | 1/1989 | Owen et al. |
| 4,817,631 A | 4/1989 | Schnepp-Pesch et al. |
| 4,820,504 A | 4/1989 | Battifora |
| 4,834,943 A | 5/1989 | Yoshiyama |
| 4,839,194 A | 6/1989 | Malluche et al. |
| 4,849,173 A | 7/1989 | Chang |
| 4,870,975 A | 10/1989 | Cronk et al. |
| 4,887,612 A | 12/1989 | Esser et al. |
| 4,893,982 A | 1/1990 | Yamaguchi |
| 4,961,432 A | 10/1990 | Guirguis |
| 4,962,036 A | 10/1990 | Cermak et al. |
| 4,971,783 A | 11/1990 | Bolton et al. |
| 4,971,912 A | 11/1990 | Buhl et al. |
| 4,984,355 A | 1/1991 | Lubrano et al. |
| 4,985,206 A | 1/1991 | Bowman et al. |
| 4,997,100 A | 3/1991 | Dudek |
| 5,002,184 A | 3/1991 | Lloyd |
| 5,009,088 A | 4/1991 | Cislo |
| 5,024,830 A | 6/1991 | Linner |
| 5,047,008 A | 9/1991 | de Juan, Jr. et al. |
| 5,057,546 A | 10/1991 | Sudan |
| 5,077,012 A | 12/1991 | Guirguis |
| 5,080,869 A | 1/1992 | McCormick |
| 5,115,816 A | 5/1992 | Lee |
| 5,127,537 A | 7/1992 | Graham |
| 5,132,758 A | 7/1992 | Minami et al. |
| 5,137,710 A | 8/1992 | Smalley et al. |
| 5,143,714 A | 9/1992 | Cosgrove et al. |
| D330,257 S | 10/1992 | Schneider |
| 5,170,800 A | 12/1992 | Smith et al. |
| 5,172,700 A | 12/1992 | Bencini et al. |
| 5,217,479 A | 6/1993 | Shuler |
| 5,224,488 A | 7/1993 | Neuffer |
| 5,272,093 A | 12/1993 | Silva et al. |
| 5,284,753 A | 2/1994 | Goodwin, Jr. |
| 5,308,758 A | 5/1994 | Dahl |
| 5,312,758 A | 5/1994 | Ahlqvist |
| 5,318,589 A | 6/1994 | Lichtman |
| 5,340,551 A | 8/1994 | Berry, Jr. |
| 5,350,150 A | 9/1994 | Fiore |
| 5,354,370 A | 10/1994 | Schmehl |
| 5,360,828 A | 11/1994 | Morrison |
| 5,411,885 A | 5/1995 | Marx |
| 5,427,742 A | 6/1995 | Holland |
| 5,533,642 A | 7/1996 | Lafond et al. |
| 5,586,438 A | 12/1996 | Fahy |
| 5,609,827 A | 3/1997 | Russell et al. |
| 5,650,327 A | 7/1997 | Copeland et al. |
| 5,665,398 A | 9/1997 | McCormick |
| 5,683,786 A | 11/1997 | Kavanaugh |
| 5,702,185 A | 12/1997 | Heikal |
| 5,718,916 A | 2/1998 | Scherr |
| 5,817,032 A | 10/1998 | Williamson, IV et al. |
| 5,867,102 A | 2/1999 | Souder et al. |
| 5,919,553 A | 7/1999 | Kavanaugh |
| 5,928,934 A * | 7/1999 | McCormick ............... 435/284.1 |
| 5,963,368 A | 10/1999 | Domanik et al. |
| 5,968,436 A | 10/1999 | Takezaki |
| 6,017,476 A | 1/2000 | Renshaw |
| 6,148,878 A | 11/2000 | Ganz et al. |
| 6,193,102 B1 | 2/2001 | Bevirt et al. |
| 6,207,408 B1 | 3/2001 | Essenfeld et al. |
| 6,289,682 B1 | 9/2001 | Rada |
| 6,387,653 B1 | 5/2002 | Voneiff et al. |
| 6,395,234 B1 | 5/2002 | Hunnell et al. |
| 6,395,373 B2 | 5/2002 | Conti et al. |
| 6,411,434 B1 | 6/2002 | Eastman et al. |
| 6,486,783 B1 | 11/2002 | Hausladen et al. |
| 6,489,171 B1 | 12/2002 | Aghassi et al. |
| 6,495,104 B1 | 12/2002 | Unno et al. |
| 6,498,032 B1 | 12/2002 | Clements et al. |
| 6,513,673 B2 | 2/2003 | Alley |
| 6,560,837 B1 | 5/2003 | Hodjat et al. |
| 6,797,928 B2 | 9/2004 | Giberson et al. |
| 7,005,110 B2 | 2/2006 | Taft et al. |
| 7,156,814 B1 | 1/2007 | Williamson, IV et al. |
| 7,179,424 B2 | 2/2007 | Williamson, IV et al. |
| 2001/0000487 A1 | 4/2001 | Essenfeld et al. |
| 2002/0030598 A1 | 3/2002 | Dombrowski et al. |
| 2002/0196146 A1 | 12/2002 | Moore |
| 2003/0021021 A1 | 1/2003 | Branch |
| 2003/0119200 A1 | 6/2003 | Taft et al. |
| 2003/0122673 A1 | 7/2003 | Anderson |
| 2003/0156996 A1* | 8/2003 | Delorme ....................... 422/102 |
| 2004/0032330 A1 | 2/2004 | Hoffman |
| 2004/0203089 A1 | 10/2004 | Fischer |
| 2005/0084425 A1 | 4/2005 | Williamson, IV et al. |
| 2005/0100981 A1 | 5/2005 | Bjornsen |
| 2005/0112034 A1 | 5/2005 | McCormick |
| 2005/0137272 A1 | 6/2005 | Gaserod et al. |
| 2005/0147538 A1 | 7/2005 | Williamson, IV et al. |
| 2005/0226770 A1 | 10/2005 | Allen et al. |
| 2007/0116612 A1 | 5/2007 | Williamson, IV |
| 2007/0166834 A1 | 7/2007 | Williamson, IV et al. |
| 2008/0138854 A1 | 6/2008 | Williamson |

FOREIGN PATENT DOCUMENTS

| | | |
|---|---|---|
| EP | 0351988 A2 | 1/1990 |
| EP | 0357228 A1 | 3/1990 |
| EP | 0471534 A2 | 2/1992 |
| EP | 1321757 A2 | 6/2003 |
| GB | 865889 A | 4/1961 |
| GB | 1483574 A | 8/1977 |
| GB | 2278441 A | 11/1994 |
| JP | 62067424 | 3/1987 |
| JP | 11132923 A | 5/1999 |
| JP | 2001296220 A | 10/2001 |
| KR | 100458860 B1 | 11/2004 |
| WO | 8600407 A1 | 1/1986 |
| WO | 00/19897 A1 | 4/2000 |
| WO | 03040697 A1 | 5/2003 |
| WO | 2004028693 A1 | 4/2004 |

(56) References Cited

FOREIGN PATENT DOCUMENTS

| WO | 2004029584 A1 | 4/2004 |
|----|---------------|--------|
| WO | 2005037182 A2 | 4/2005 |

OTHER PUBLICATIONS

European Patent Office, Supplementary European Search Report in EP Application No. 98951995, Dec. 20, 2007.
U.S. Patent and Trademark Office, International Search Report and Written Opinion in PCT Application Serial No. PCT/US07/25253, Mar. 13, 2008.
U.S. Patent and Trademark Office, Office Action in U.S. Appl. No. 11/010,773, Apr. 2, 2009.
U.S. Patent and Trademark Office, Office Action in U.S. Appl. No. 11/553,120, Apr. 10, 2009.
European Patent Office, Supplementary European Search Report in EP Application Serial No. EP04794852, Apr. 21, 2008.
European Patent Office, European Search Report in EP Application No. 08013740, Oct. 23, 2008.
European Patent Office, Supplementary European Search Report in EP Application No. 02773621, Sep. 2008.
Japanese Patent Office, Office Action in Japanese Application No. 2004-539746, Aug. 1, 2007.
Japanese Patent Office, Office Action in Japanese Application No. 2004-539747, Jul. 24, 2007.
U.S. Patent and Trademark Office, Office Action in U.S. Appl. No. 11/072,119, Jul. 1, 2009.
Nicholas G. Genes et al., Effect of substract mechanics on chondrocyte adhesion to modified alginate surfaces, Archives of Biochemistry and Biophysics 422, (2004) 161-167.
Alexi A. Wright M.D., et al., Bar Coding for Patient Safety, The New England Journal of Medicine, 353;4, Jul. 28, 2005, 3 pgs.
Healthcare Informatics, The Latest in Products and Services, Bar Coding/RFID, www.healthcare-informatics.com, Nov. 2005, 1 pg.
Sakura Finetek U.S.A., Inc., Tissue-Tek(R) TEC(TM) 5, Tissue Embedding Console System, Brochure, 2001.

* cited by examiner

CASSETTE FOR HANDLING AND HOLDING TISSUE SAMPLES DURING PROCESSING, EMBEDDING AND MICROTOME PROCEDURES, AND METHODS THEREFOR

This application is a divisional of U.S. application Ser. No. 10/963,315, filed on Oct. 12, 2004 which claims the benefit of U.S. Application Ser. No. 60/512,147, filed on Oct. 17, 2003 and generally relates to PCT application serial numbers PCT/US02/30779 and PCT/US02/30775, and the disclosures of which are hereby fully incorporated by reference herein.

FIELD OF THE INVENTION

The present invention generally relates to supports for handling and embedding tissue samples for pathological analysis and, more particularly, to cassettes which can receive one or more tissue samples and be embedded and subsequently microtomed with the tissue sample or samples.

BACKGROUND OF THE INVENTION

To accurately diagnose various tissue diseases and conditions, medical personnel must remove one or more samples of tissue from the body of a patient. This process of harvesting tissue from the body is known as a biopsy. Once the tissue sample or samples are removed and sent to a pathology laboratory, the tissue will go through a series of procedures performed by a histotechnician and, ultimately, a pathologist, in order to diagnose the tissue. The present invention generally relates to those procedures that are normally performed by the histotechnician to prepare the tissue sample or samples into slides that may be analyzed under a microscope by the pathologist.

Although the singular term "sample" is used throughout this specification, it should be understood that this term likewise encompasses plural "samples" as well. Once a tissue sample is removed from the body of a patient, it is typically placed into a specimen container containing a tissue fixative solution and then the container is transported to a pathology laboratory. The tissue will undergo a process known as "grossing-in" in the pathology lab during which a histotechnician will retrieve the tissue sample from the container, typically cut the tissue into appropriate sizes for tissue processing, place individual samples into the appropriate sized small plastic tissue cassettes, and assign tracking numbers to each cassette. These tracking numbers are then logged into a tracking system used in the laboratory. For the smallest tissue samples, which may only be scrapings, the cassette will have fine mesh openings on the sides and bottoms. In other situations involving very small tissue samples, the samples are placed into a bag that resembles a tea bag and prevents the smallest tissue samples from escaping. Larger tissue samples are placed into cassettes having somewhat larger slotted openings which are again smaller than the tissue sample inside the cassette.

The cassettes are then placed into a stainless steel perforated basket and run through a tissue processing machine, often overnight. This machine uses a combination of vacuum, heat, and chemicals to remove the interstitial fluids. Once the fluids have been removed from the tissue samples, the processing machine immerses the tissues samples in a bath of molten paraffin so that the interstices in the tissue are replaced with paraffin. The histotechnician then removes the basket from the machine and removes the individual tissue cassettes. At an embedding station, which has a molten paraffin reservoir and dispenser, the histotechnician will individually remove the tissue from each cassette. The histotechnician must carefully orient the tissue sample, based on tissue type, into a stainless steel base mold which is roughly the size of the tissue cassette and is partially filled with molten paraffin. The tissue sample must be manually held, typically using forceps, against the bottom of the mold. If it is not, this could compromise the ability to make proper slices of the tissue later in the microtome. The molten paraffin is then rapidly cooled on a refrigerated plate, which may be a thermal electric cooler (TEC), to partially solidify the paraffin thereby holding the tissue sample in the proper orientation against the bottom of the mold. The cassette is then placed on top of the base mold and paraffin is poured through the opened top of the cassette into the base mold. The cassette changes its function at this point in the procedure from a tissue holding component to a fixation device for later use in taking shavings or slices from the solidified paraffin in a microtome. The base mold is chilled until all of the molten paraffin has solidified and the histotechnician removes the stainless steel base mold from the block of embedded paraffin. The tissue sample is thus embedded within a rectangular block of paraffin with a plastic tissue cassette on the opposite side which will then be used as a holder in the chuck of the microtome. As with the tissue processing machine, the embedding process is accomplished in a batch fashion during which an average histotechnician may embed approximately 40 to 60 cassettes per hour.

The blocks of hardened paraffin containing the embedded tissue samples are then ready to be sliced into extremely thin sections for placement on a microscope slide. The histotechnician mounts the embedded tissue block in a chuck on the microtome which is sized to accept the side of the block that has the embedded plastic cassette. The histotechnician can then begin slicing the paraffin block which has the tissue sample embedded opposite to the plastic cassette surface. This yields a ribbon of individual slices of the tissue embedded in the paraffin. The action of the microtome causes the individual slices to stick together when done properly and, subsequently, these very thin ribbons of slices are floated into a water bath and a glass slide is carefully placed underneath the slice. The slice, with the thin sectioned tissue sample embedded therein, is then adhered to the top of the slide.

When the histotechnician has enough slides from the tissue sample, the slides are placed into an automatic staining machine. The staining machine goes through a series of infiltrating steps to stain the different tissue and cells of the slide different colors. This helps the pathologist identify different structures and makes it easier to find any abnormalities in the tissue. After the staining procedure is complete, the slides are cover slipped and prepared for the pathologist to place under a microscope to analyze.

Based on the summary of the procedure provided above, it will be appreciated that conventional tissue sample handling and processing is a very labor-intensive process involving several manual steps performed by a histotechnician. Thus, repetitive stress injuries such as carpal tunnel syndrome are prevalent. This is especially true with the tissue sample embedding process. These multiple manual operations and repeated tissue handling increase the likelihood of human error and, moreover, require highly trained and skilled histotechnicians to ensure that the tissue samples ultimately adhered to the slides for analysis by the pathologist are in an optimum condition and orientation to make accurate diagnoses.

U.S. Pat. No. 5,817,032 (the '032 patent) discloses various improvements to this area of technology, including new manners of holding tissue samples during the grossing in, embedding, and microtome or slicing procedures. More specifically, the '032 patent relates to a tissue trapping and supporting device, which may be a cassette, and which may be cut with a microtome. When a cassette is used, the tissue sample is immobilized within the cassette and subjected to the process for replacing tissue fluids with paraffin. Then, the tissue sample and the cassette are sliced at the same time for mounting on microscope slides. Because the tissue sample is never removed from the cassette from the time it is processed in the tissue processing machine to the time that it is cut with the microtome, a significant amount of handling time is saved. Moreover, the chance for human error or tissue loss due, for example, to dropping the tissue during handling, is significantly reduced due to the elimination of separate tissue handling steps. This patent also generally discusses an automated process which, in conjunction with the novel tissue cassettes, even further reduces the handling steps during the entire procedure.

In spite of the various advances made in this field, there is an increasing need for additional improvements related to further manners to ease the handling procedures of tissue samples, increasing production capability and increasing the quality of the embedded tissue samples and the resulting slices or ribbons of embedded tissue which will be subject to diagnosis.

SUMMARY OF THE INVENTION

The present invention generally provides a cassette for holding a tissue sample. The cassette includes a body and may also include a lid. The body comprises a bottom wall and one or more side walls extending upwardly with respect to the bottom wall to define an interior space for receiving the tissue sample. In one aspect, a plurality of query points (e.g., sensing elements) are associated with the body and/or lid and configured to allow an automated sensing system to determine at least one characteristic of the cassette. The characteristic may be size, shape, or some other structural or functional characteristic. The cassette preferably includes a lid configured to be coupled with the body and movable between open and closed positions. A flange extends along upper portions of at least two of said side walls and the sensing elements may be located on the flange. The sensing elements can further comprise holes or other detectable, computer readable characteristics or elements. The detection can take place in a contact or non-contact manner. This inventive aspect can also or alternatively be applied to a frame member which holds the cassette during processing and/or embedding. The bottom wall of the cassette body preferably transitions to the plurality of side walls with a radiused corner. The bottom wall further includes a plurality of holes having shapes which are radially elongate and/or widen in a direction toward the plurality of side walls generally from a gate or fill location of the cassette body in a mold used to manufacture the cassette. Each of these features can help guide the flow of material for forming the cassette during an injection molding process. The holes in the bottom wall are preferably located generally at the center of the bottom wall and have a teardrop shape and/or oval shape.

At least two of the side walls are positioned in opposed relation to one another and the dimension between the opposed side walls varies along the length of the opposed side walls. This may be the result of angling, undulating or radiusing the side walls along their length and assists with making slices in a microtome more easily. As examples, the side walls may be angled starting at one end thereof and ending at an opposite end, or starting at a location between opposite ends thereof and ending, respectively, at the opposite ends.

In another aspect, a stop member in the interior space of the cassette is configured to stop the lid at a minimum distance from the upper surface of the bottom wall. The stop member may be part of the cassette body or part of the lid.

In another embodiment, an orientation cassette includes a plurality of posts extending upwardly from the bottom wall. The posts are configured to orient the tissue sample therebetween to ensure that the sections taken with the sample are most appropriate for diagnostic purposes. The lid receivable in the interior space includes holes for removably receiving the posts. The posts are further arranged so as not to be aligned with one another in a straight line either perpendicular or parallel to any one of the side walls. This helps ensure more effective cutting in a microtome and less dulling of the microtome blade.

These and other objectives, advantages and features will become more readily apparent to those of ordinary skill in the art upon review of the following detailed description of the preferred embodiments taken in conjunction with the accompanying drawings.

DETAILED DESCRIPTION

Cassette Configuration/Type Sensing

Figures 1, 1A:
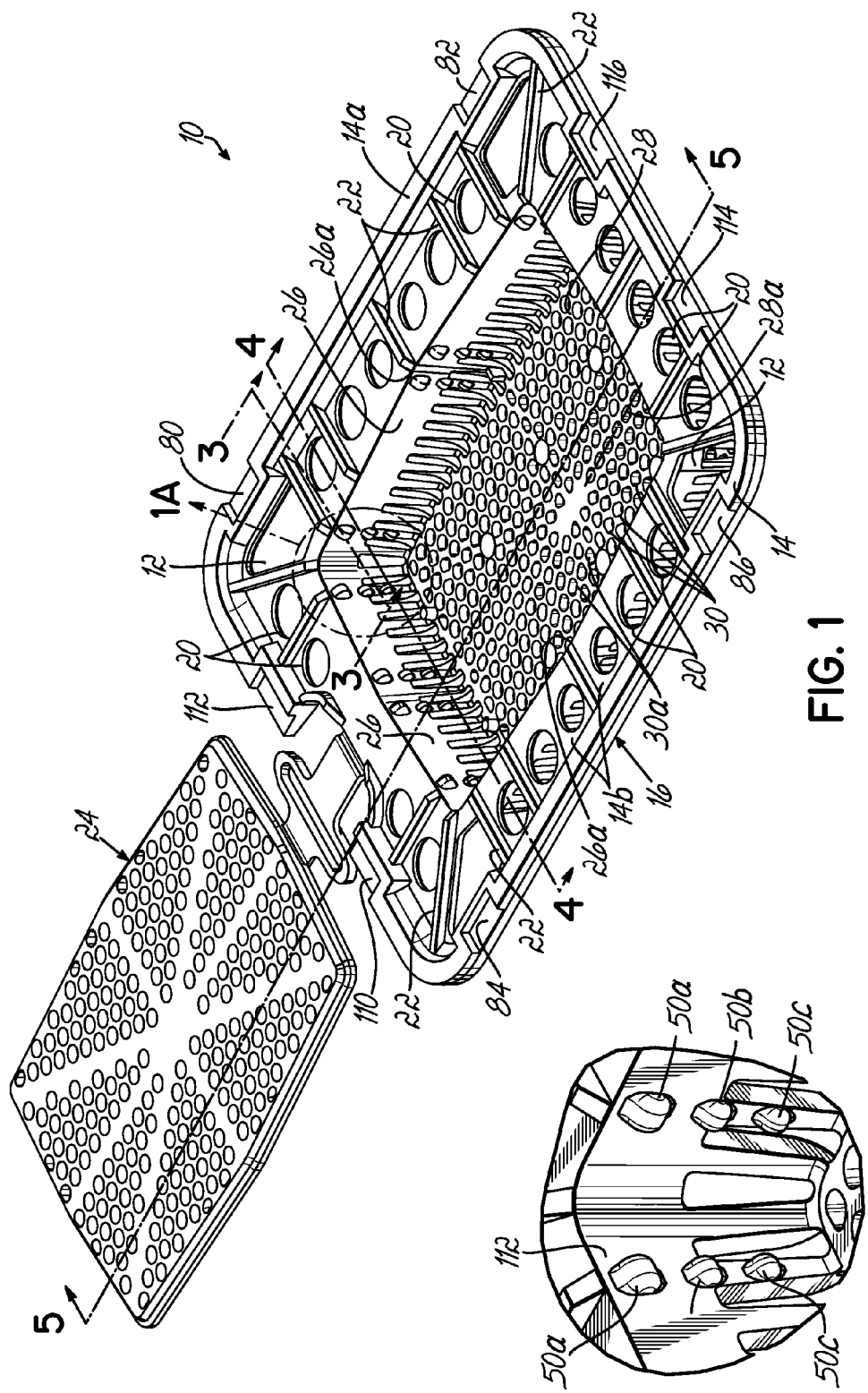
FIG. 1 is a perspective top view of an illustrative biopsy cassette constructed in accordance with the invention.
FIG. 1A is an enlarged view of encircled portion 1A taken from FIG. 1.
Figure 2:
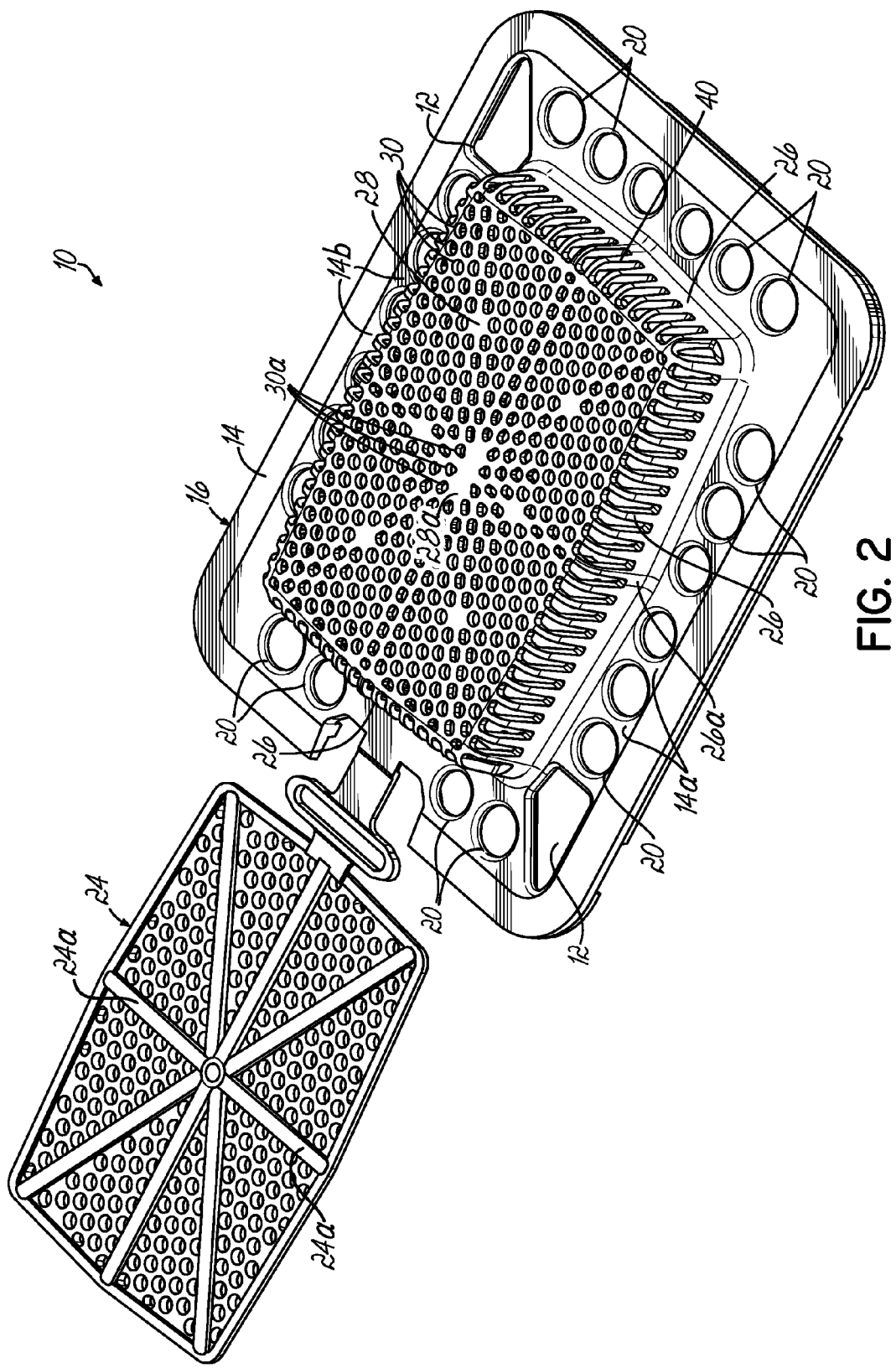
FIG. 2 is a perspective bottom view of the biopsy cassette shown in FIG. 1.
Figure 5:
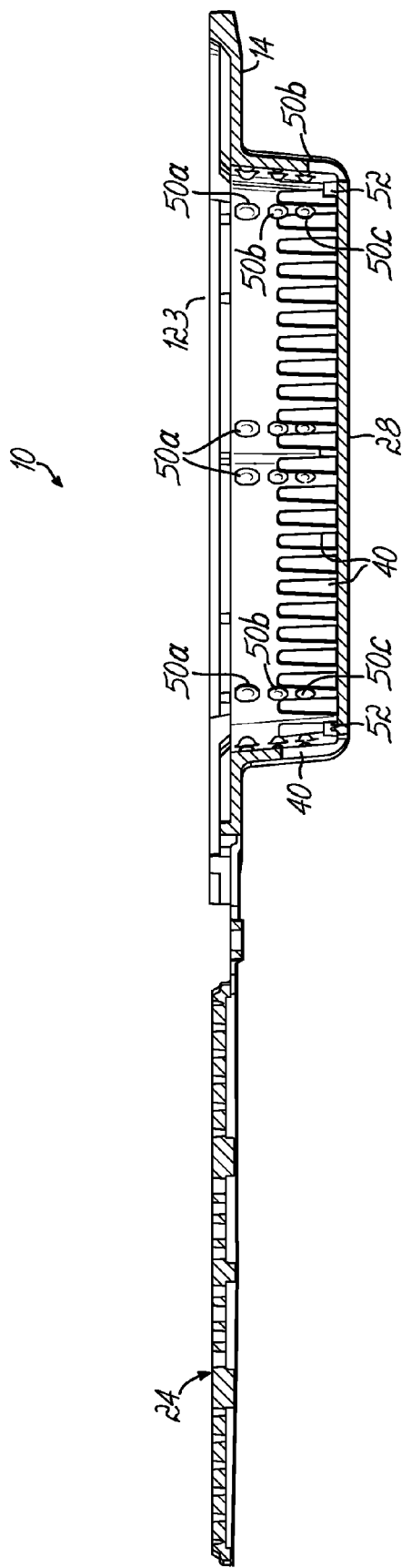
FIG. 5 is a sectional view taken generally along line 5-5 of FIG. 1.

Referring to FIGS. 1 and 2, cassette 10 may be used in an automated embedding apparatus such as the one disclosed in the above incorporated PCT application serial number PCT/US02/30779. More specifically, the apparatus can utilize an opto-electronic identification feature that allows a robotic system to determine which of at least two types of cassettes 10 has been extracted from an input basket. The different types of cassettes 10 may, for example, be of different size or have other differing characteristics and/or function. A plurality of query points, which may be holes 12 placed in a flange 14 at the periphery of the cassette body 16, allows an optical scanner to be used to give a binary signal at each query point on the cassette 10. Since it is advantageous at this time for all cassettes 10 to use the same embedding frame, all cassettes 10 are designed to fit into the interior of the frame with a similar registration in the up and down positions. As additional cassette features are developed or customer identification becomes necessary, for example, a similar sensing feature may be incorporated into the frame which receives the cassette 10. This feature may be incorporated into many different types of cassettes to be used in conjunction with automated machinery.

In co-pending application PCT/US02/30779 a sensor can query each cassette 10 after it has been removed from the input basket. A robotic arm moves the cassette 10 in the frame under a single sensor head. This sensor detects the cassette presence to make certain that the cassette 10 has not been dropped or improperly grasped from the input basket and is more specifically detecting a binary (signal vs. no signal) to communicate with the machine control to proceed to embed the cassette 10. This feature may be enhanced such that the sensor and control proceed to determine how to process the cassette 10 based on cassette size, type and/or other parameters. Other parameters may include the type of base mold and any special heating or cooling parameters that are necessary for processing and/or embedding a particular type of cassette. The sensor is used to query each cassette/frame assembly at each input location of, for example, a plurality of locations where the control has been programmed to check for a signal. As mentioned above, four holes 12 at the corners of the flange 14 are currently used for the input locations. Center portions 14a, 14b of the cassette flange 14 could be used to increase the number of possible cassette configurations the machine can discern. As discussed below, the corner locations of holes 12 allow three cassette configurations to be detected and includes a redundant routine since the cassette 10 is symmetrical and could be installed by an operator in two different orientations within the frame (not shown) which carries the cassette 10 throughout the process. There must be a high degree of certainty that the automated machinery has correctly detected and verified the cassette configuration. Using a redundant sensing area is one way to facilitate improved certainty.

The sensor in the preferred embodiment is an emitter/detector sensor, whereby a sensing light beam (infrared or other color spectrum) is directed towards a tuned sensor. If the query point is open (e.g., a hole 12 in the cassette flange 14 is detected) the emitter receives enough signal to register. If the query point is opaque or diffuse (e.g., no hole 12 detected) the tuned sensor will not receive enough light to register a signal. Since the cassette assemblies are pre-processed in a tissue processor which involves the use of a paraffin containing solution, there is a possibility of a meniscus of paraffin blocking one of the sensor holes 12. The sensor holes 12 can be formed large enough to minimize this possibility.

In addition, the cassette 10 is rectangular with two long sides and two short sides and, as mentioned, can be installed in the frame in two different orientations along the long axis of the cassettes 10. The sensing configuration is designed to take this into account, that is, the configuration allows the machine to discern the three cassette types regardless of the orientation of the cassette 10 in the frame. Each long side supplies enough information to properly detect the cassette type and the other long side carries redundant information. If more than three configurations are required, then additional sensing holes (not shown) may be placed on either side of the centerline at the edges.

Figure 8:
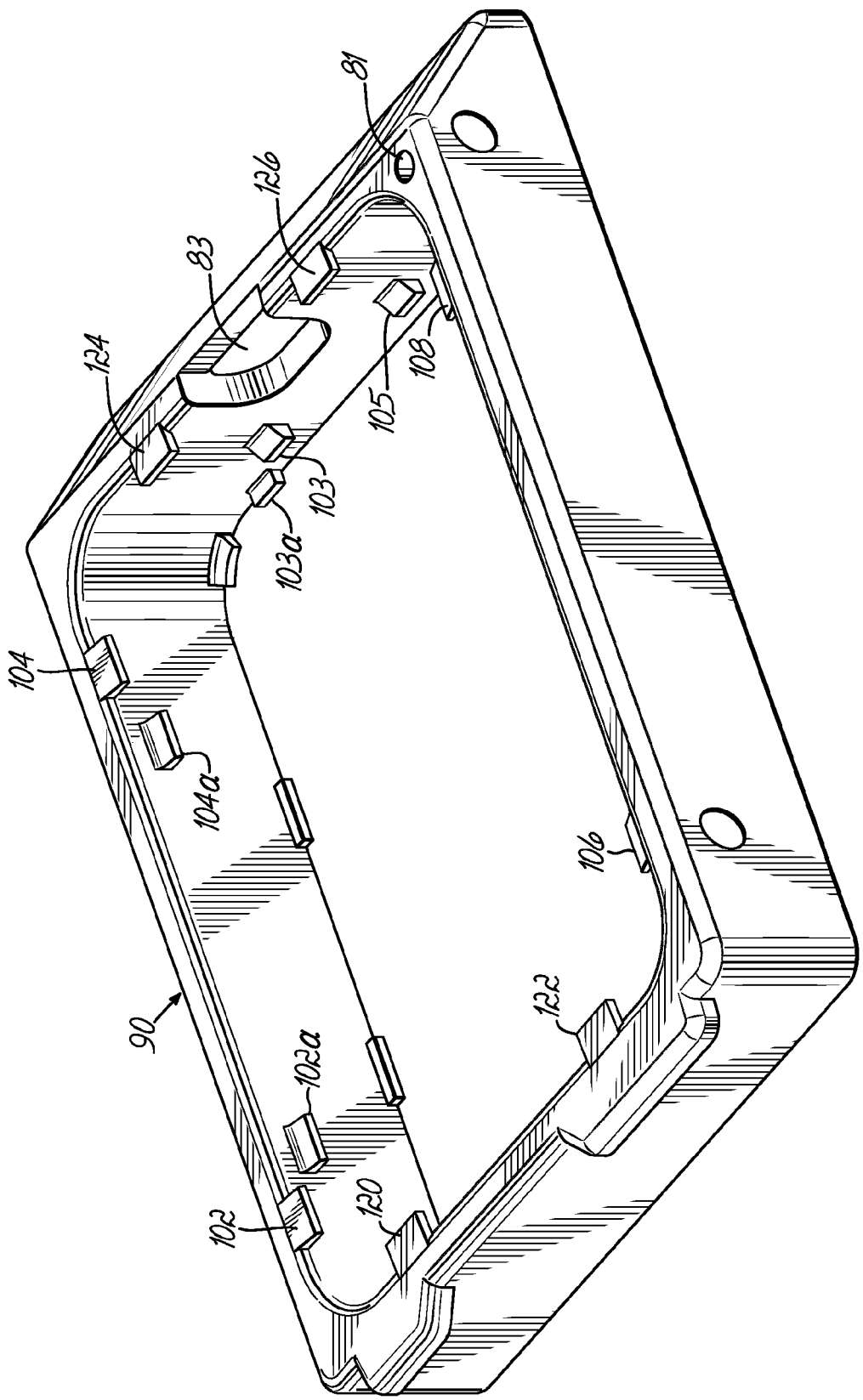
FIG. 8 is a perspective view of a frame member constructed in accordance with the invention and adapted to carry a cassette.

With regard to the actual sensing plan it is as follows for three possible cassettes:
Large Tissue Cassette:
All corners opaque (no holes 12)
Signal: Both sensors off
Biopsy Cassette (Small Cassette) 10:
Opposite corners are opaque (no holes 12), other corners are open (holes 12) (diagonal symmetry)
Signal: One sensor on, one off (order insensitive)
Orientation Cassette:
All corners are open (holes 12)
Signal: Both sensors on It will be appreciated that many different types of sensing systems, which involve either a contact or non-contact type sensor, may be used to carry out the inventive concepts explained above. For example, many different types of optical sensing systems, magnetic sensing systems, barcode type systems or RFID type systems may be used to allow proper identification of the cassette and/or frame or other forms of information retrieval by the control of an automated embedding and/or processing system. As one additional example, a frame member 80 is shown in FIG. 8 which includes an RFID element 81 embedded therein to allow appropriate embedded information to be relayed to the control system, for example, of an automated processing and/or embedding apparatus. The information to be conveyed is also wide ranging and may include, for example, various diagnostic information, patient history, tissue sample information, or any other information helpful to the histologic or pathologic process.

Securement of Cassette Within Frame Member

Referring to FIGS. 1 and 8, a plurality of depressions 80, 82 and 84, 86 are formed on the top surfaces of flange 14 along the long sides of cassette body 16. A frame member 90 (FIG. 8) is used to carry cassette 10 and depressions 80, 82 and 84, 86 respectively receive projections or tabs 102, 104 and 106, 108. Additional depressions 110, 112 and 114, 116 are formed on the upper surfaces of flange 14 along the short sides of cassette body 16. These depressions respectively receive projections or tabs 120, 122 and 124, 126 formed within the frame member 90. The registered tabs and depressions securely maintain the cassette 10 within the frame member 90 during processing and embedding operations.

In the embodiment shown, frame member 90 includes upper sets of tabs 102, 102a, 104, 104a for supporting a cassette 10 at a first position within the frame member 90 during initial processing of a tissue sample. Corresponding lower sets of tabs 103, 103a, 105 are provided to support the cassette 10 at a second position for embedding the tissue sample in paraffin, as described more fully in the above incorporated PCT/US02/30775. More specifically, and as shown and described in PCT/US02/30775, frame member 90 includes a through opening defining a space for removably receiving the cassette 10. As shown in FIG. 8, the tabs or projections 102, 102a, 104, 104a and 103, 103a, 105 extend into the through opening of the frame member 90. The cassette 10 is insertable into the through opening on one side of the frame member 90 and retained in the first position within the frame member 90 by upper tabs or projections 102, 102a, 104, 104a. The cassette 10 is movable to the second position in which the sectionable bottom wall 28 (FIG. 4) of the cassette body 16 and the tissue sample are moved out from the through opening and exposed on an opposite side of the frame member 90. As stated above, the cassette 10 is retained in the second position by tabs or projections 103, 103a, 105. In the second position, the frame member 90 is adapted to support the cassette 10 for embedding in paraffin. After the tissue sample within the cassette 10 has been embedded in paraffin, the cassette 10 and frame member 90 are removed from the embedding mold, and frame member 90 may be used to fix the assembly within a microtome chuck (not shown) so that slices may be taken from the paraffin embedded, sectionable cassette 10 and tissue sample.

Air Removal During Embedding Process

The tissue embedding process, when performed manually with conventional cassettes, is subject to steps or technique that dislodge or reduce the entrapment of air bubbles in the paraffin (or embedding material) block. Air bubbles are detrimental because they can weaken the paraffin block and subsequent microtome sectioning can "break out" or cleave off the main paraffin body. This leaves an inconsistent edge or hole in the "ribbon" of sections which must flow successively from the section in the microtome process. This can result in an unsuccessful ribbon, and poor quality slides for diagnosis. One way to lessen the presence of air bubbles is to tap or otherwise rapidly move the cassette assembly to remove air bubbles. However, with high speed automated embedding, the machine may not be designed to perform such a step. Therefore, in locations where air could accumulate the largest possible holes may be provided to allow the air to escape during the paraffin-filling step. Still referring to FIGS. 1 and 2, holes 12, 20 in the flange 14 of the cassette 10 and under the writing surface of the frame are provided to allow air to escape. It will be appreciated that sensor holes 12 are therefore dual purpose. These holes 12, 20 should be large enough to allow escape of air and free of flash or burrs. Obstructions, such as ribs under the flange, may trap rising bubbles. Stiffening flanges 22 are located on the top side of the flange 14 to eliminate air entrapment. Frame member 80 also includes an air escape recess or passage 83 on its inner surface.

Material Flow to Injection Mold Cassettes.

Figure 1B:
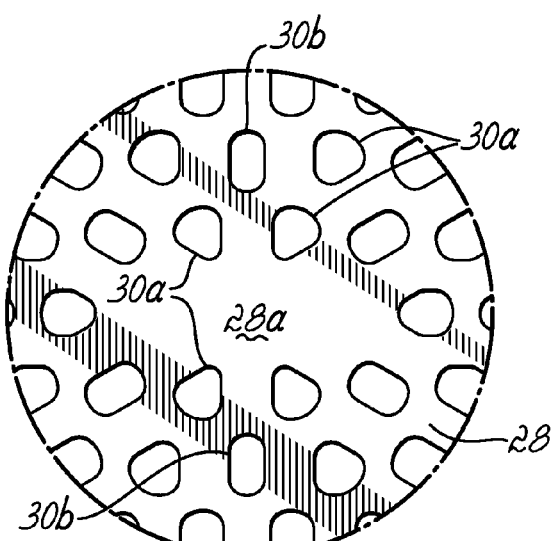
FIG. 1B is an enlarged top view of the cassette bottom wall shown in FIG. 1.

Again referring to FIGS. 1 and 2, certain features of the cassette 10 allow for effective injection molding techniques to be used in its manufacture. First, the gate for filling the mold of the cassette body 16 and the lid 24 should have flow runners directly leading to the edges of the cassette sidewalls 26. In the bottom wall 28 the cassette body 16, it is best to avoid having areas where the tissue will be blocked from the passage of fluids used to process the tissue. Although the center 28a of the bottom wall 28 has some avoidable gate section, the majority of area is covered with flow holes 30. For molding it is typically preferable to have solid flow ribs 24a as used for lid 24. In this inventive aspect, the mold pins for forming central holes 30a (FIG. 1B) are configured with a teardrop shape to direct the flow of the cassette material out to the sidewalls 26. Other mold pins for forming holes 30b are elongate in shape in a radial direction toward side walls 26. These shapes help direct cassette material efficiently away from the gate or fill location (e.g., central area 28a). The transition area 29 (FIG. 3) from the bottom wall 28 to the ribs 40 which form the side walls 26 is radiused to reduce the flow restriction for molding.

Non-Linear Side Walls

FIGS. 1 and 2 also show that the sidewalls 26 are non-linear with respect to the frame side which also determines the cutting plane of the microtome. This may mean that the side walls 26 generally angle from an approximate midpoint 26a thereof, as shown, or that the dimension between opposite sidewalls 26 changes due to angling or curving the side walls 26 in their lengthwise direction. The cassette side walls 26 could, for example, have a large radius along their length or undulate with respect to the frame sides. The objective of this feature is to avoid having a parallel sidewall with respect to the frame side to increase microtome slicing efficiency. It will be appreciated that many configurations can fulfill this objective.

Minimum Lid Engagement Height

Figure 3:
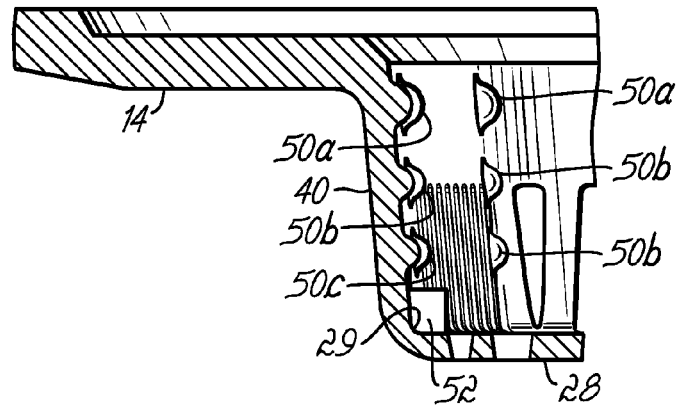
FIG. 3 is a sectional view taken generally along line 3-3 of FIG. 1.
Figure 4:
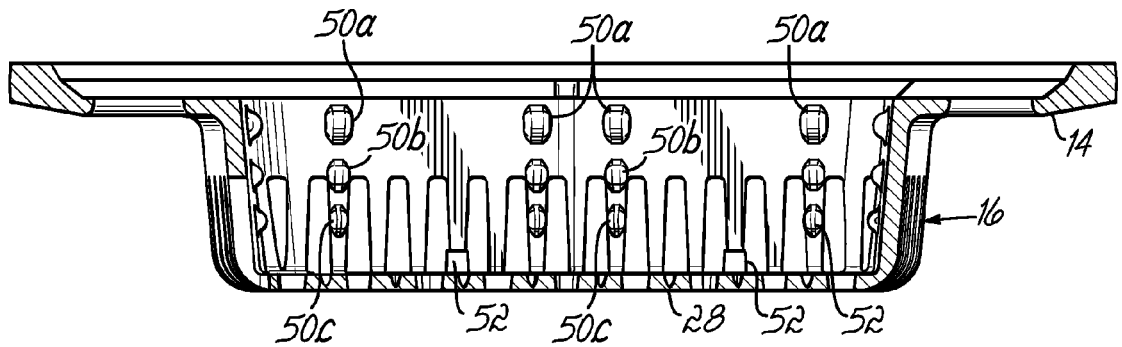
FIG. 4 is a sectional view taken generally along line 4-4 of FIG. 1.

Referring to FIGS. 1A, 3 and 4, the lid 24 engages sidewall bumps or projections 50a, 50b or 50c in order to keep the lid 24 engaged with the cassette body 16 at the appropriate height against a tissue sample thereby keeping the tissue sample enclosed and immobilized in the cassette 10 during processing. With extremely small tissue samples such as biopsy samples which can be as small as 1 mm$^3$. The lid 24 should not come down all the way and crush the fragile biopsy sample. Stops 52 are incorporated into the cassette body 16 to keep the lid 24 from closing all the way down on the sample. Alternatively, such stops could be located on the lid 24. The height of each stop 52 is about 0.75 mm but can be in the range of about 0.25 mm to about 1 mm high. Also, the extremely thin cassette bottom wall 28 (preferred to be about 0.38) allows the sample to be trapped but not to have undue compressive forces so as to cause a detrimental crush artifact to show up in the sectioned biopsy and subsequent diagnostic slides.

Orientation Biopsy Cassette

Figure 6:
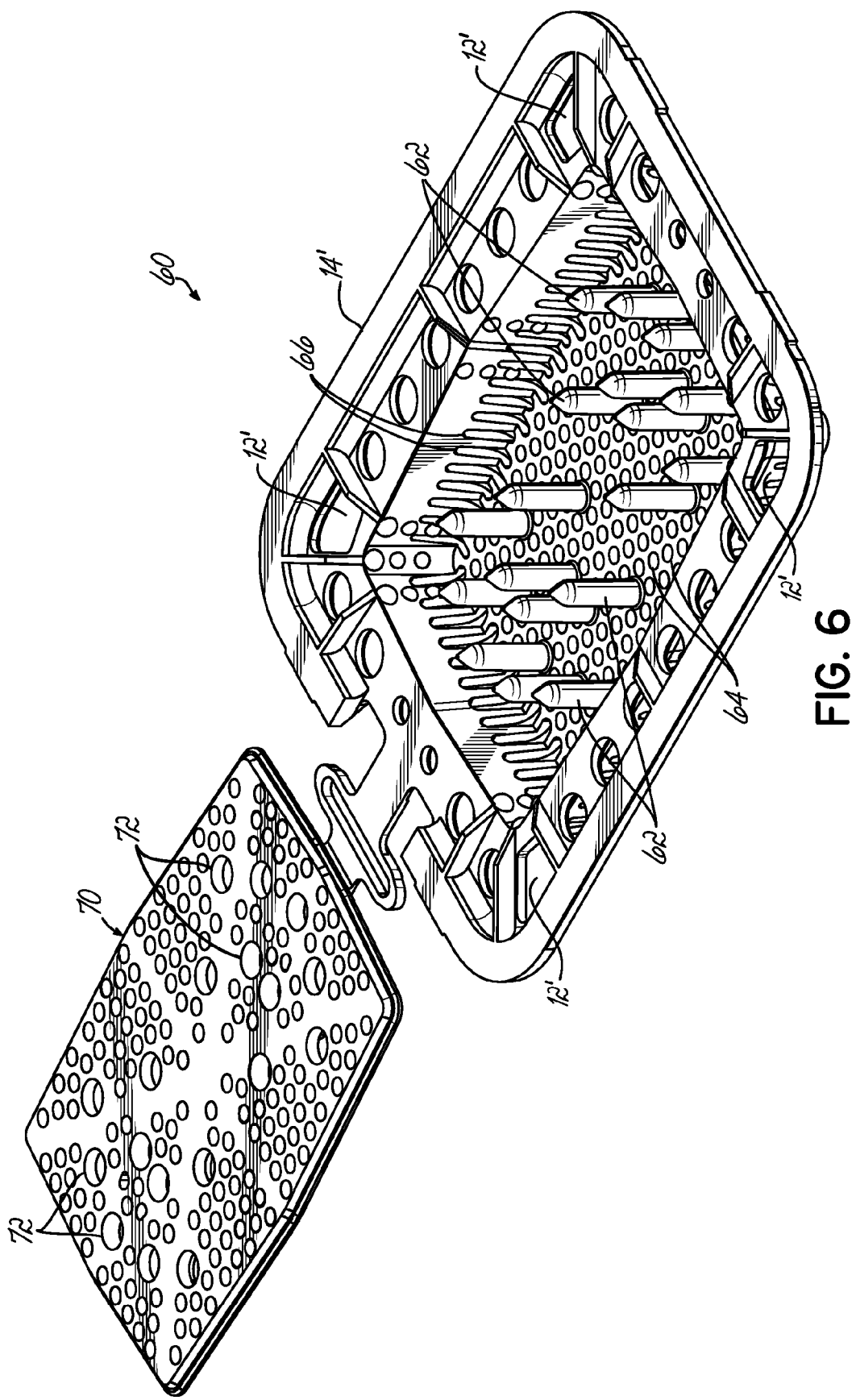
FIG. 6 is a perspective top view of an illustrative tissue orientation cassette constructed in accordance with the invention.
Figure 7:
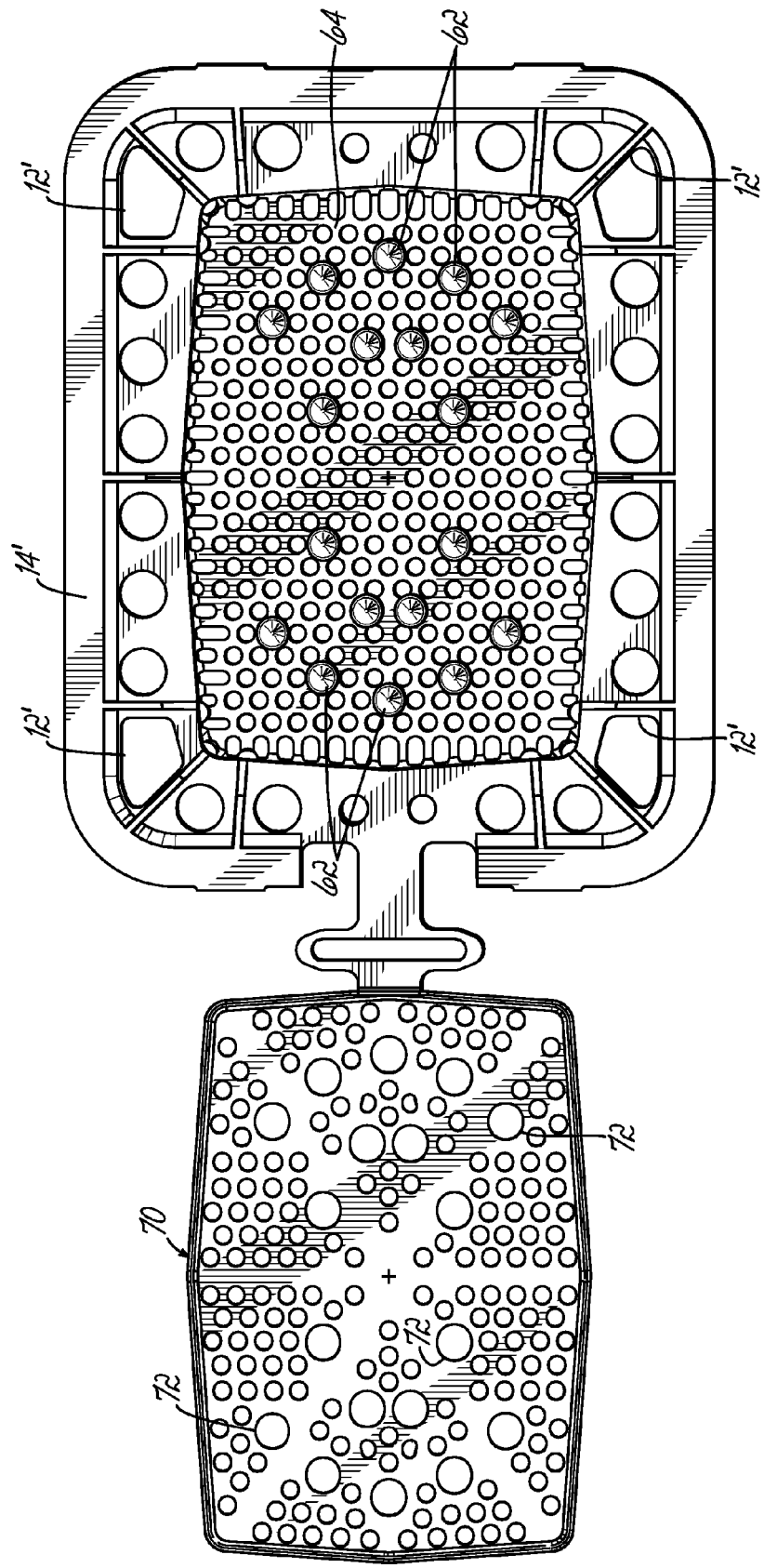
FIG. 7 is a top view of the tissue orientation cassette shown in FIG. 6.

Referring to FIGS. 6 and 7, an orientation cassette 60 is used to orient special tissues (not shown) that must be sectioned "on edge". Reference numerals corresponding to those from the first embodiment, but having prime marks in FIGS. 6 and 7 refer to corresponding elements of structure. Tissue such as skin, gal bladder, bladder, etc., needs to be oriented to allow the pathologist to view a full cross section of the biopsy. These samples can be quite small, and therefore need to be retained in a cassette with small holes like the biopsy cassette 10. The orientation biopsy cassette 60 allows the histotechnologist to place the tissue in the proper orientation for sectioning at the time of gross-in. This predetermined orientation will be maintained through the tissue processing and embedding procedures, thus maintaining the proper orientation to the cutting plane without having to remove the tissue and reorient it for sectioning in a paraffin mold. The tissue is placed between upright posts 62 molded into the bottom wall 64 of the cassette 60. These posts 62 have been arranged in configurations that take into account average thickness and lengths of the tissue to be used in the cassette 60. The posts 62 are further arranged so that they are not directly in line with one another with respect to directions either parallel to or perpendicular to the sectioning blade path. Since the posts have more plastic material in them than the sidewall ribs 66, they could cause dulling of a portion of the microtome blade at an undesirable rate after repeated use. Therefore, the posts 62 are positioned to minimize the number of posts 62 cut in succession in the same blade pass. The lid 70 of the orientation cassette 60 has corresponding clearance holes 72 for the upright posts 62. The tissue is held in place between the posts 62, and the lid 70 is depressed onto the posts 62 to secure the tissue against movement, just as in the other tissue trapping cassette configurations disclosed herein, or in the incorporated applications. There is a small clearance between the lid clearance holes 70 and the posts 62 to keep any tissue from escaping from the cassette 60.

While the present invention has been illustrated by the description of the various embodiments thereof, and while the embodiments have been described in considerable detail, it is not intended to restrict or in any way limit the scope of the appended claims to such detail. Aside from and/or in addition to the details and principles disclosed herein, the components described herein may be modified with the details or principles described in the above-incorporated PCT applications. Additional advantages and modifications will readily appear to those skilled in the art. The invention in its broader aspects is therefore not limited to the specific details, representative apparatus and methods and illustrative examples shown and described. Accordingly, departures may be made from such details without departing from the scope or spirit of Applicants' general inventive concept. The various features of the invention as set forth herein may be utilized alone or in various combinations whether or not such combinations are specifically disclosed in embodiments shown and described in the detail description.

What is claimed is:

1. An apparatus for processing a tissue sample, comprising:
a cassette for holding the tissue sample, said cassette formed from a material capable of being sectioned in a microtome and including:
a body including a bottom wall and at least one side wall extending upwardly with respect to said bottom wall to define an interior space for receiving the tissue sample, and
at least one detectable element on said cassette for detection by an automated sensing system, said detectable element representing at least one characteristic of said cassette; and
a frame having a through opening defining a space for removably receiving said cassette, said cassette being insertable into said through opening on one side of said frame and retained in a first position within said frame and movable to a second position in which the sectionable bottom wall of the cassette body and the tissue sample are moved out from the through opening on an opposite side of said frame and retained in the second position, wherein said frame is adapted to support said cassette in the microtome with said cassette retained in said second position during sectioning of the tissue sample;
wherein said at least one detectable element distinguishes said cassette from a second cassette that is configured to be removably received in said frame.

2. The apparatus of claim 1, further comprising a lid configured to be coupled with said body and movable between open and closed positions, said lid being stiffer than said bottom wall.

3. The apparatus of claim 1, further comprising:
a flange extending along an upper portion of said side wall, said flange including said at least one detectable element.

4. The apparatus of claim 3, wherein at least two of said detectable elements comprise holes.

5. The apparatus of claim 1, wherein at least two of said detectable elements comprise holes.

6. An apparatus for processing a tissue sample, comprising:
a cassette for holding the tissue sample, said cassette formed from a material capable of being sectioned in a microtome and including:
a body including a bottom wall and at least one side wall extending upwardly with respect to said bottom wall to define an interior space for receiving the tissue sample, and
a flange extending along an upper portion of said side wall, said flange including at least one hole; and
a frame having a through opening defining a space for removably receiving said cassette, said cassette being insertable into said through opening on one side of said frame and retained in a first position within said frame, and said cassette movable to a second position in which the sectionable bottom wall of the cassette body and the tissue sample are moved out from the through opening on an opposite side of said frame and retained in the second position, wherein said frame is adapted to support said cassette in the microtome with said cassette retained in said second position during sectioning of the tissue sample;
wherein said at least one hole distinguishes said cassette from a second cassette that is configured to be removably received in said frame.

7. An apparatus for processing a tissue sample, comprising:
a cassette for holding the tissue sample, said cassette formed from a material capable of being sectioned in a microtome and including:
a body including a bottom wall and at least one side wall extending upwardly with respect to said bottom wall to define an interior space for receiving the tissue sample,
a lid configured to be coupled with said body, and
at least one detectable element associated with at least one of said body or said lid and configured to allow an automated sensing system to determine at least one characteristic of said cassette; and
a frame having a through opening defining a space for removably receiving said cassette, said cassette being insertable into said through opening on one side of said frame and retained in a first position within said frame, and said cassette movable to a second position in which the sectionable bottom wall of the cassette body and the tissue sample are moved out from the through opening on an opposite side of said frame and retained in the second position, wherein said frame is adapted to support said cassette in the microtome with said cassette retained in said second position during sectioning of the tissue sample;
wherein said at least one detectable element distinguishes said cassette from a second cassette that is configured to be removably received in said frame.

8. The apparatus of claim 1, wherein said frame further comprises first and second sets of projections to respectively retain said cassette in said first and second positions.

9. The apparatus of claim 6, wherein said frame further comprises first and second sets of projections to respectively retain said cassette in said first and second positions.

10. The apparatus of claim 7, wherein said frame further comprises first and second sets of projections to respectively retain said cassette in said first and second positions.

* * * * *